United States Patent [19]

Olney

[11] Patent Number: 4,833,138
[45] Date of Patent: May 23, 1989

[54] PHENOTHIAZINEALKANEAMINES FOR TREATMENT OF NEUROTOXIC INJURY

[75] Inventor: John W. Olney, Ladue, Mo.

[73] Assignee: Washington University, St. Louis, Mo.

[21] Appl. No.: 112,660

[22] Filed: Oct. 23, 1987

[51] Int. Cl.⁴ .............................................. A61K 31/54
[52] U.S. Cl. .............................. 514/226.2; 514/225.5; 514/225.8; 514/225.2
[58] Field of Search ......................................... 514/223

[56] References Cited

PUBLICATIONS

Gordon, Psychopharmacological Agents, vol. II (1967), pp. 3-30.

Primary Examiner—Stanley J. Friedman
Attorney, Agent, or Firm—J. Timothy Keane; Paul D. Matakaitis

[57] ABSTRACT

Compounds, compositions and methods of treatment are described to control brain damage associated with anoxia or ischemia which typically follows such conditions as stroke, cardiac arrest or perinatal asphyxia. The treatment includes administration of a phenothiazinealkaneamine compound as an antagonist to inhibit excitotoxic actions at major neuronal excitatory amino acid receptor sites. Compounds of most interest are those of the formula

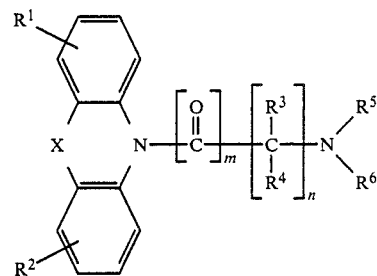

wherein each of $R^1$ and $R^2$ is hydrido; wherein each of $R^3$ and $R^4$ is independently selected from hydrido, methyl and ethyl; wherein each of $R^5$ and $R^6$ is independently selected from methyl, ethyl and n-propyl; wherein X is sulfur; wherein m is zero; and wherein n is two.

8 Claims, No Drawings

PHENOTHIAZINEALKANEAMINES FOR TREATMENT OF NEUROTOXIC INJURY

FIELD OF THE INVENTION

This invention is in the field of clinical neurology and relates specifically to compounds, compositions and methods for neuroprotective purposes such as controlling brain damage which occurs during periods of anoxia or ischemia associated with conditions such as stroke, cardiac arrest or perinatal asphyxia.

BACKGROUND OF THE INVENTION

Unlike other tissue which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which was early characterized as a fast excitatory transmitter in the mammalian brain. Glutamate is also known as a powerful neurotoxin capable of killing CNS neurons under certain pathological conditions which accompany stroke and cardiac arrest. Normally, high glutamate concentrations are maintained inside cells of the CNS by energy-dependent transport systems, but high concentrations are not allowed in the extracellular compartment where glutamate can exert excitotoxic action at excitatory synaptic receptors. Under low energy conditions such as hypoglycemia, hypoxia or ischemia, cells release glutamate and, because of the energy deficiency, the transport systems are unable to move glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by the specific antagonism of postsynaptic glutamate receptors [see S. M. Rothman and J. W. Olney, "Glutamate and the Pathophysiology of Hypoxia—Ischemic Brain Damage," *Annals of Neurology*, Vol. 19, No. 2 (1986)]. Glutamate receptors, also known as excitatory amino acid (EAA) receptors, are of three types, each being named after the EAA glutamate analogue which selectively excites them, namely: Kainate (KA), N-methyl-D-aspartate (NMDA or NMA) and quisqualate (QUIS). Glutamate is believed to be a mixed (broad spectrum) agonist capable of binding to and exciting all three EAA receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia which occurs in conditions such as stroke, cardiac arrest or perinatal asphyxia.

Phencyclidine (PCP) and the PCP-like compound ketamine have been found to reduce selectively the excitatory effects of NMDA as compared to KA and QUIS [Anis, N.A. et al, "The Dissociative Anaesthetics, Ketamine and Phencyclidine, Selectively Reduce Excitation of Central Mammalian Neurones by N-Methyl-Aspartate", *Br. J. Pharmacol.*, 79, 565 (1983)]. Blocking of NMA neurotoxicity by PCP and ketamine has been demonstrated [J. W. Olney et al., "The Anti-Excitotoxic Effects of Certain Anesthetics, Analgesics and SedativeHypnotics," *Neuroscience Letters*, 68, 29–34 (1986)].

A correlation has been found between the PCP binding effects of some PCP-derivative stereoisomers and NMDA antagonism. For example, the stereoselective effects of cis-N-(1-phenyl-4-methylcyclohexyl)piperidine and (+)-1-(1-phenylcyclohexyl)-3-methylpiperidine [(+)-PCMP] over each of their corresponding isomer counterparts in reducing the excitatory action of NMDA have been confirmed in binding and behavioral data [S. D. Berry et al, "Stereoselective Effects of Two Phencyclidine Derivatives on N-Methylaspartate Excitation of Spinal Neurons in the Cat and Rat", *Eur. J. Pharm.*, 96, 261–267 (1983)]. Also, the compound (+)-PCMP has been found to be a potent inhibitor of the specific binding of [$^3$H]PCP to rat cerebral cortical membranes [M. E. Goldman et al, "Differentiation of [$^3$H]Phencyclidine and (+)-[$^3$H]SKF-10,047 Binding Sites in Rat Cerebral Cortex", *FEBS Lett.*, 170, 333–336 (1985)]. It has also been shown that PCP and NMA receptors are co-localized throughout much of the mammalian forebrain [W. Maragos et al, "High Correlation between the Localization of [$^3$H]TCP Binding and NMDA Receptors", *Eur. J. Pharmacol.*, 123, 173–174 (1986)].

The compound MK-801 {(+)-5-methyl-10,11-dihydro-5H-dibenzo[a,d]cyclohepten-5,10-imine maleate)} has been found to be a potent, selective non-competitive antagonist of the N-methyl-D-aspartate receptor site [E. H. F. Wong et al, "The Anticonvulsant MK-801 Is A Potent N-Methyl-D-Aspartate Antagonist", *Proc. Nat'l. Acad. Sci U.S.A.*, Vol. 83, pp. 7104–7108 (Sept. (1986)].

Well-known competitive NMA antagonists, such as D-α-amino-5-phosphonopentanoate, are capable of effectively blocking the excitotoxic effects of NMA. But such compounds show little therapeutic promise in treatment or prevention of ischemic brain damage because these compounds do not penetrate the blood-brain barrier.

Phenothiazinealkaneamines and derivatives have been described for various pharmaceutical purposes. For Example, ethopropazine is an anti-cholinergic useful in treatment of Parkinsonism [L. S. Goodman et al, "*The Pharmacological Basis of Therapeutics*, 5th Edn. Macmillan (1975)]. The compound 2-propionyl-10-[2-(dimethylaminopropyl]phenothiazine is mentioned in a study of the interaction of certain tranquilizers and antihistamines on bacterial cells [A. M. Shibl et al, *J. Pharm. Sci.*, 73(b), 841–843 (1984)]. The compound N,N-diethyl-3-methyl-10H-phenothiazine-10-ethanamine monohydrochloride is mentioned in a study of phenothazine derivatives as inhibitors of gastric acid secretion [A. Canas-Rodriguiz et al, *An. Quim., Ser. C.*, 80 (1), 39–41 (1984)]. The compound 1-[10-[2-(dimethylaminoethyl]-10H-phenothiazin-2-yl]ethanone is mentioned in a study of derivatives of 2-phenothiazin-2'-ylcinchoninic acid having potential analgesic-antiinflammatory activity [F. Savelli, *Chim. Ind.* (*Milan*), 59(4), 300 (1977)]. The compound 2-chloro-N,N-diethyl-10H-phenothiazine-10-ethanamine monohydrochloride is mentioned in a study of the correlation between neuroleptic activity and the anticholinesterase property of some phenothiazine derivatives [J. Legheand et al, *Ann. Pharm. 'Fr.*, 31(9–10), 613–622 (1973)]. The compound dimethothiazine methanesulfonate is mentioned for prevention of death from ulcer and shock in Japanese Patent Application Kokai 56/26817 (March 1981). The compound 10-[2,3-bis(dimethylamino)propyl]-phenothiazine is mentioned in a study of the effect of neuroleptics, tranquilizers, narcotics, antidepressants and anticonvulsive drugs on the alteration of mouse behavior caused by acetaldehyde [L. M. Andronova et al, *Drug Alcohol Depend.*, 8(2), 85–92 (1981)]. The compound 10-[2-(dimethylaminopropyl] -N,N-dimethyl-10H-phenothiazine-2-sulfonamide methanesulfonate is mentioned in a study of the effects of some drugs on the rigidity of the cat due to ischemic or intercollicular decerebration [D. R. Maxwell et al, *Neuropharmacology*, 11, (6), 849 –855 (1972)].

DESCRIPTION OF THE INVENTION

Control of excitotoxic neuropathological processes and the neurodegenerative consequences thereof in mammals is provided by treating a susceptible mammal with an anti-excitotoxic effective amount of a compound of a class phenothiazinealkaneamines represented by Formula I:

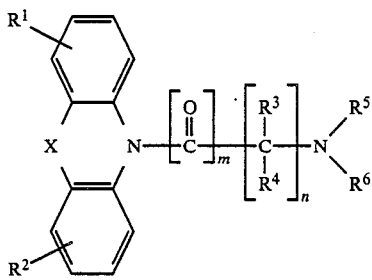

wherein each of $R^1$ and $R^2$ is one or more groups independently selected from hydrido, hydroxyalkyl, haloalkyl, acyl, cycloalkyl, cycloalkylalkyl, haloalkylsulfonyl, alkylcarbonyl, halo, alkylthio, phenylalkyl, phenylalkylthio, cyano, nitro, amino, alkylamino, sulfono, alkylaminosulfonyl, amido, alkylamido, hydroxyimino, hydroxyiminoalkyl, carboxyl, carboxylalkyl, carboxyalkenyl, thiazolyl, methylthiazolyl, alkoxycarbonylamino, alkylaminosulfonylamino, aminocarbonyliminoalkyl, haloalkylcarbonyl, morpholinoalkylcarbonyl, aminothiazolyl, morpholinothiocarbonylalkyl, dioxycycloalkylalkyl, cyclopropylcarbonyl, tetrazolylalkyl, iminoalkyl and hydroxyiminoalkyl; wherein each of $R^3$ through $R^6$ is independently selected from hydrido, alkyl, alkoxy, alkenyl, hydroxyalkyl, alkylaminoalkylcarbonyl, alkoxyalkyl, glycyl, aminoalkyl, alkylaminothioalkyl, aminoalkylcarbonyloxy, cyano, phenylalkyl, phenylalkyloxyalkyl, cycloalkyl, haloalkyl, morpholinoalkylalkyl, piperazinylalkyl, azepinylalkyl, phenylalkylaminoalkylamido, alkylaminocarbonyloxyalkyl, piperidinylalkyl and piperidinylalkylaminoalkylcarbonyl; wherein X is selected from sulfur, sulfinyl and sulfonyl; wherein m is zero or one; and wherein n is an integer from one through five.

A preferred class of compounds within Formula I consists of those compounds wherein each of $R^1$ and $R^2$ is one or more groups independently selected from hydrido, alkyl, alkoxy, hydroxyl, aldehyde, hydroxyalkyl, haloalkyl, acyl, cycloalkyl, cycloalkylalkyl, haloalklylsulfonyl, alkylcarbonyl, halo, alkythio, phenalkyl, phenalkylthio, nitro, amino, alkylamino, sulfono, alklaminosulfonyl, amido, alkylamido, hydroxyimino, hydroxyiminoalkyl, carboxyl, carboxylalkyl, carboxyalkenyl, thiazolyl, methylthiazolyl, alkoxycarbonylamino, alkylaminosulfonylamino, aminocarbonyliminoalkyl, haloalkylcarbonyl, morpholinoalkylcarbonyl, aminothiazolyl, morpholinothiocarbonylalkyl, dioxycycloalkylalkyl, cyclopropylcarbonyl, tetrazolylalkyl, iminoalkyl and hydroxyiminoalkyl; wherein each of $R^3$ and $R^4$ is independently selected from hydrido, alkyl, alkoxy, alkenyl, hydroxyalkyl, alkylaminoalkylcarbonyl, alkoxyalkyl, glycyl, aminoalkyl, haloalkyl, alkylaminothioalkyl, aminoalkylcarbonyloxy and cyano; wherein each of $R^5$ and $R^6$ is independently selected from hydrido, alkyl, alkoxy, hydroxyalkyl, benzyl, haloalkyl, alkoxyalkyl, alkoxycarbonyl, cycloalkyl, morpholinoalkyl, piperizinylalkyl, azepinylalkyl, alkenyl, phenylalkoxyalkyl, phenylalkylaminoalkylamido, alkylaminocarbonyloxyalkyl, piperidinylalkyl, piperidinylaminoalkyl and piperidinylalkylaminoalkylcarbonyl; wherein X is sulfur; wherein m is zero or one; and wherein n is an integer from one through four.

A more preferred class of compounds within each of $R^1$ and $R^2$ is one or more groups independently selected from hydrido, alkyl, alkoxy, hydroxyl, hydroxyalkyl, haloalkyl, alkylthio, alkoxycarbonyl, cyano, amino and alkylamino; wherein each of $R^3$ and $R^4$ is independently selected from hydrido, alkyl, hydroxyalkyl, alkenyl, haloalkyl, aminoalkyl and cyano; wherein each of $R^5$ and $R^6$ is independently selected from hydrido, alkyl, haloalkyl, cycloalkyl, benzyl, and alkoxyalkyl; wherein m is zero; wherein X is sulfur; and wherein n is an integer from one through three.

An even more preferred class of compounds within Formula I consists of those compounds wherein each of $R^1$ and $R^2$ is one or more groups independently selected from hydrido, methyl, ethyl, n-propyl, isopropyl, n-butyl, sec-butyl, iso-butyl, tert-butyl, acetyl, trifluoromethyl, methoxycarbonyl and ethoxycarbonyl; wherein each of $R^3$ and $R^4$ is independently selected from hydrido, methyl, ethyl, n-propyl, isopropyl, n-butyl, sec-butyl, iso-butyl, tert-butyl, hydroxyethyl, trifluoromethyl, 2,2,2-trifluoroethyl, perfluorethyl, aminomethyl and aminoethyl; wherein each of $R^5$ and $R^6$ is independently selected from hydrido, methyl, ethyl, n-propyl, isopropyl, n-butyl, sec-butyl, iso-butyl and tert-butyl; wherein X is sulfur; wherein m is zero; and wherein n is one or two.

A most preferred class of compounds within Formula I consists of those compounds wherein each of $R^1$ and $R^2$ is hydrido; wherein each of $R^3$ and $R^4$ is independently selected from hydrido, methyl and ethyl; wherein each of $R^5$ and $R^6$ is independently selected from methyl, ethyl and n-propyl; wherein X is sulfur; wherein m is zero; and wherein n is two.

Within this most preferred class of compounds of Formula I is the following group of particularly-preferred compounds:
10-[2,3-bis(dimethylamino)propyl]phenothiazine;
10-[2,3-bis(dimethylamino)propyl]phenothiazine hydrochloride;
10-[2-(dimethylamino)propyl]phenothiazine;
10-[2-(dimethylamino)propyl]phenothiazine hydrochloride; and
10-[2-(diethylamino)ethyl]phenothiazine (commonly known as "phenopropazine" or "ethopropazine").

Of this group of particularly-preferred compounds of Formula I, ethopropazine and its hydrochloride salt are of most interest.

Other specific compounds of interest within Formula I are as follows:

N-(diethylaminoethyl)thiodiphenylamine;
2-propionyl-10-[2-dimethylamino)propyl]phenothiazine;
10-[2-(dimethylamino)ethyl]-2-(trifluoromethyl)-phenothiazine;
10-(N,N-dimethylglycyl)phenothiazine;
2-chloro-10-[2-(dimethylamino)propyl]phenothiazine;
10-[(diethylamino)acetyl]-10H-phenothiazine; N,N,α-trimethyl-2-(methylthio)thiophenothiazine-10-acetamide;
2-cyclopropyl-10-[2-(diethylamino)ethyl]phenothiazine;
10-[2-[methyl(α-methylphenethyl)amino]ethyl]phenothiazine;
2-(cyclopropylmethyl)-10(N,N-dimethylglycyl)-phenothiazine maleate;
10-[2-(diethylamino)ethyl]-2-[(trifluoromethyl)sulfonyl]phenothiazine;
10-[2-[[2-(benzyloxy)ethyl]ethylamino]ethyl]-2-(trifluoromethyl)phenothiazine;
2-chloro-β-[(dimethylamino)methyl]-phenothiazine-10-ethanol monohydrochloride;
2-cyclopropyl-N,N,α-trimethyl-10H-phenothiazine-10-ethanamine;
2-[ethyl[2-[2(trifluoromethyl)phenothiazin-10-yl]ethyl]amino]ethanol;
10-(N,N-dimethylnorleucyl)phenothiazine;
N,N,α-trimethyl-2-[(2-methylpropyl)thio]-10H-phenothiazine-10-ethanamine;
10-[2-(dimethylamino)ethyl]-2-(isopropylthio)-phenothiazine;
10-[2-(dimethylamino)ethyl]-2-(ethylthio)phenothiazine;
2-(butylthio)-N,N-diethyl-α-methyl-10H -phenothiazine-10-ethanamine hydrochloride;
N,N,α-trimethyl-2-[(phenylmethyl)thio]-10H -phenothiazine-10-ethanamine;
10-[2-(dimethylamino)propyl]-N,N-dimethyl-10H-phenothiazine-3-sulfonamide;
10-[2-(dimethylamino)propyl]-phenothiazine 5-oxide monohydrochloride;
10-[2-(dimethylamino)-1-methylethyl]-phenothiazine monomethosulfate;
1-[10-[2-(dimethylamino)-1-methylethyl]phenothiazin-3-yl]-1-propanone hydrochloride;
N,N,β-trimethyl-10H-phenothiazine-10-ethanamine diethyl sulfate;
10-(N,N-dimethyl-2-phenylglycyl)phenothiazine;
3,7-dibromo-10-[2-(dimethylamino)propyl]phenothiazine5,5-dioxide;
3,7-dibromo-10-[2-(dimethylamino) ethyl]-phenothiazine5,5-dioxide;
10-[2-(dimethylamino)ethyl]-7-nitro-phenothiazin-3-ol-5,5-dioxide;
10-[2-(dimethylamino)ethyl]-7-hydroxy-phenothiazine-3-sulfonic acid-5,5-dioxide;
2,2'[(2-phenothiazin-10-ylethyl)imino]di-ethanol;
N,N-diethyl-1-phenothiazin-10-ylthio-formamide;
10-[2-(dimethylamino)propyl]-N,N-dimethyl-10-H-phenothiazine-2-sulfonamide methanesulfonate;
10-[2-(dimethylamino)propyl]-2-methoxy-phenothiazine5-oxide;
10-[2-(dimethylamino)propyl]-2-methoxyphenothiazine;
10-[2-(dimethylamino)ethyl]-N,N-dimethylphenothiazine2-sulfonamide maleate;
10-[2-(dimethylamino)ethyl]-2-phenothiazinecarbonitrile; 10-[2-(dimethylamino)ethyl]-2-phenothiazinecarbonitrile 5-oxide;
10-[2-(dimethylamino)propyl]phenothiazine-2-carbonitrile;
2-(2-amino-4-thiazolyl)-10-[2-(dimethylamino)propyl]-phenothiazine;
10-[2-(dimethylamino)propyl]phenothiazin-2-yl-morpholinomethyl ketone;
10-[2-(dimethylamino)-1-methylethyl]-phenothiazine5,5-dioxide;
10-[2-(dimethylamino)propyl]-phenothiazine-2-sulfonamide;
1-[10-[2-(dimethylamino)ethyl]phenothiazin-3-yl-1-butanone;
ethyl methyl(2-phenothiazin-10-ylpropyl)carbamate-S,S-dioxide;
10-[2-(dimethylamino)propyl]-phenothiazine-5,5-dioxide tartrate;
10-[2-(dimethylamino)propyl]-N,N-dimethyl-phenothiazine-2-sulfonamide oxide;
10-[2-[bis(2-chloroethyl)amino]ethyl]-3-methoxyphenothiazine monohydrochloride;
10-[N-(3-morpholinopropyl)sarcosyl]phenothiazine;
10-[N-[3-(4-methyl-1-piperazinyl)propyl]sarcosyl]-phenothiazine;
10-[N-[3-(hexahydro-1H-azepin-1-yl)propyl]sarcosyl]-phenothiazine;
N,N-diethyl-phenothiazine-10-carboxamide;
4[[10-[2-(dimethylamino)ethyl]phenothiazin-2-yl]thioacetyl]morpholine monohydrochloride;
10-[2-(dimethylamino)ethyl]-phenothiazine-2-acetic acid monohydrochloride;
2-chloro-N-methyl-N-[2-[methyl(2-phenylethyl)amino[ethyl]10H-phenothiazine-10-carboxamide;
10-[2-(dimethylamino)propyl]-10H -phenothiazine-2-carboxaldehyde;
N,N,α-trimethyl-2-(4-methyl-2-thiazolyl)-10H-phenothiazine-10-ethanamine;
N,N-diethyl-3-methyl-10H-phenothiazine-10-ethanamine monohydrochloride;
N,N-bis[2-[[(methylamino)carbonyl]oxy]ethyl]-10H-phenothiazine-10-carboxamide;
methyl[10-[2-(dimethylamino)ethyl]-10H -phenothiazin-2yl]carbamate;
N'-[10-[2-(dimethylamino)propyl]-10H -phenothiazin-2-yl]-N,N-dimethyl-sulfamide;
4-[[2-(2-chloro-10H-phenothiazin-10-yl)ethyl]methylamino]2,2,6,6-tetramethyl-1-piperidinyloxy;
3-[10-[2-(dimethylamino)propyl]-10H -phenothiazin-2-yl]2-propenoic acid;
2-(cyclopropylmethyl)-10-[2-(dimethylamino)ethyl]-phenothiazine;
10-[2-(dimethylamino)ethyl]-1-ethyl-phenothiazine;
10-[2-(dimethylamino)ethyl]-N-methyl-phenothiazine2-carboxamide;
1-[10-[2-(dimethylamino)propyl[phenothizin-2-yl]-1-propanone;
10-[2-dimethylamino)ethyl]-N-ethyl-phenothiazine-2-carboxamide;
10-(N-2-piperidinoethylsarcosyl)phenothiazine;
10-[2-(dimethylamino)propyl]-2-(methylthio)phenothiazine;

10-[2-(dimethylamino)propyl]-phenothiazine-2-carboxaldehyde;
2-tert-butyl-10-[2-(dimethylamino)-1-methylethyl]-phenothiazine;
10-[2-(dimethylamino)ethyl]-2-pentylphenothiazine;
10-[2-(dimethylamino)-1,1-dimethylethyl]--(methylthio)phenothiazine;
10-[N-[2-(dimethylamino)ethyl]sarcosyl]phenothiazine;
10-[2-(dimethylamino)propyl]phenothiazine-2-carboxaldehyde semicarbazone;
chloromethyl 10-[2-(dimethylamino)ethyl]phenothiazin-2-yl-ketone hydrochloride;
2-[2-(chloromethyl)-1,3-dioxolan-2-yl]-10-[2-(dimethylamino)ethyl]phenothiazine hydrochloride;
cyclopropyl 10-[2-(dimethylamino)propyl]phenothiazin-2-yl-ketone methiodide;
N,N,α-trimethyl-2-[1-methyl-1-(1H-tetrazol-5-yl)ethyl10H-phenothiazine-10-ethanamine;
10-[2-(dimethylamino)propyl]-α,α-dimethyl-10H-phenothiazine-2-acetonitrile;
10-(2-dimethylaminoethyl)phenothiazin-2-yl methylketoneoxime;
β-dimethylaminophenothiazine-10-butyronitrile;
10-[2-(diallylamino)ethyl]phenothiazine;
2-(dimethylamino)-10-[2-(dimethylamino)ethyl]phenothiazine maleate;
10-(2-dimethylamino-1-methylethyl)-2-phenylphenothiazine;
N,N-dicyclohexyl-phenothiazine-10-carboxamide;
10-(2-diethylaminoethyl)-2,8-dimethoxyphenothiazine;
2-chloro-10-[2-[(4-ethoxybutyl)ethylamino]ethyl]-phenothiazine;
10-[2-[ethyl(2-piperidinoethyl)amino]propyl]phenothiazine, dihydrochloride;
10-[2-(dimethylamino)propyl]-α,α-dimethyl-10H-phenothiazine-2-acetic acid monohydrochloride.

The term "hydrido" denotes a single hydrogen atom (H) which may be attached, for example, to a carbon atom or to an oxygen atom to form an hydroxyl group. Where the term "alkyl" is used, either alone or within other terms such as "haloalkyl" and "hydroxyalkyl", the term "alkyl" embraces linear or branched radicals having one to about ten carbon atoms. Preferred alkyl radicals are "lower alkyl" radicals having one to about five carbon atoms. The term "cycloalkyl" embraces radicals having three to about ten carbon atoms, such as cyclopropyl and cyclobutyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as a bromochloromethyl group. Examples of a polyhaloalkyl are trifluoromethyl, 2,2,2-trifluoroethyl, perfluoroethyl and 2,2,3,3-tetrafluoropropyl groups. The terms "alkylol" and "hydroxyalkyl" embrace linear or branched alkyl groups having one to ten carbon atoms any one of which may be substituted with one or more hydroxyl groups. The term "alkenyl" embraces linear or branched radicals having two to about ten carbon atoms and containing at least one carbon-carbon double bond. The term "alkynyl" embraces linear or branched radicals having two to about ten carbon atoms and containing at least one carbon-carbon triple bond. The terms "alkoxy" and "alkoxyalkyl" embrace linear or branched oxycontaining radicals having alkyl portions of one to ten carbon atoms, such as methoxy group. The "alkoxy" or "alkoxyalkyl" radicals may be further substituted with one or more halo atoms, such as fluoro, chloro or bromo, to provide haloalkoxy or haloalkoxyalkyl groups.

Specific examples of alkyl groups are methyl, ethyl, n-propyl, isopropyl, n-butyl, sec-butyl, iso-butyl, tert-butyl, n-pentyl, iso-pentyl, methyl-butyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within the family of compounds of Formula I, are the tautomeric forms of the described compounds, isomeric forms including diastereomers, and the pharmaceutically-acceptable salts thereof. The term "pharmaceutically-acceptable salts" embraces salts commonly used to form alkali metal salts and to form addition salts of free acids or free bases. Since the compounds of Formula I contain basic nitrogen atoms, such salts are typically acid addition salts. The nature of the salt is not critical, provided that it is pharmaceutically acceptable, and acids which may be employed to form such salts are, of course, well known to those skilled in this art. Examples of acids which may be employed to form pharmaceutically acceptable acid addition salts include such inorganic acids as hydrochloric acid, sulphuric acid and phosphoric acid and such organic acids as maleic acid, succinic acid and citric acid. Other salts include salts with alkali metals or alkaline earth metals, such as sodium, potassium, calcium and magnesium, or with organic bases, such as dicyclohexylamine. All of these salts may be prepared by conventional means from the corresponding compound of Formula I by reacting, for example, the appropriate acid or base with the compound of Formula I.

Methods of synthesis of the phenothiazinealkaneamine compounds of Formula I are known. For example, preparation of the compound ethopropazine is described in U.S. Pat. No. 2,607,773.

BIOLOGICAL EVALUATION

Prevention of the neurodegenerative consequences associated with conditions of hypoxia or ischemia may be accomplished with administration of a compound of Formula I. In particular, the compound ethopropazine was evaluated in biological assays designed to detect compounds capable of inhibiting hypoxia/ischemia-induced neuronal degeneration. Ethopropazine was evaluated for its ability to inhibit the binding of the PCP ligand tritiated 1-[1-(2-thienyl)cyclohexyl]piperidine [$^3$H-TCP].

NMDA/KA Antagonist Assay

A 15-day old chick embryo retina, incubated for 30 min. in a balanced salt solution (BSS) containing 1 mM Glu, developed a full lesion resembling that described in the immature mouse retina following s.c. administration of Glu. Other excitotoxin agonists also produce acute lesions within 30 min., each agent being effective at a concentration proportional to its known excitatory and toxic potencies. The pattern of cellular degeneration is restricted in each case to the ganglion cell, inner plexiform and inner nuclear layers, but within these areas certain agonists induce different patterns of degeneration, the differences being most pronounced between NMA and KA. Two agonists were employed in the present test, each at a concentration established previously to be the lowest concentration required to consistently cause a fully-developed retinal lesion: KA (25 μM) and NMA (200 μM). Ethopropazine was tested at various concentrations for its ability to prevent KA or NMA neurotoxicity. Although partial blocking was sometimes observed for antagonist concentrations below the threshold for complete protection, the criterion used for comparing agents for antagonist potency was the concentration required to completely prevent KA or NMA from exerting any toxic activity in any specimen (n>6) studied at that concentration. Internal controls in each experiment consisted of at least six specimens being incubated with agonist alone. A typical toxic reaction had to be present in all controls and absent from all experimental specimens in order to qualify as a blocking effect. The method of tissue preparation was as follows: 15-day old chick embryos were decapitated and their eyes removed and cut into quadrants after excising the cornea and removing the lens, vitreous and iris. The retinal quadrants were then gently separated from the pigment epithelium and incubated for 30 min. at 37° C. in BSS to which an agonist or agonist plus antagonist was added. The BSS contained 140 mM $Na^+$, 5.0 mM $K^+$, 0.5 mM $Ca^{++}$, 4 5mM $Mg^{++}$, 150 mM $Cl^-$, 5.6 mM glucose and bicarbonate/phosphate buffer (pH 7.3). After incubation for 30 min., the retinal quadrants were fixed by immersion in phosphatebuffered solution containing 1.5% glutaraldehyde and 1% paraformaldehyde, then additionally fixed in 1% osmium tetroxide, dehydrated in graded ethanols, cleared in toluene and embedded in araldite. Sections were cut 1 μM thick on a Sorval ultratome and stained with Methylene blue/Azure 11 for histopathological evaluation by light microscopy. Blocking of KA toxicity by ethopropazine was not observed, but at a concentration of 25.0 μM, ethopropazine provided total protection against toxicity of NMA at 200 μM concentration.

Receptor Binding Assay

For receptor binding, frozen brain sections (10 microns) were incubated in 5 μM tris acetate (pH 7.25) containing 0.5 mM magnesium acetate and 20 nM $^3$H-TCP for 45 min. at 4° C. Non-specific binding was assessed with 200 μM PCP. Inhibition of $^3$H-TCP binding was studied by including potential inhibitors in the $^3$H-TCP incubation at concentrations from 10 nM to 1 mM. Dissociation and inhibition constants were calculated by Scatchard/Rosenthal analysis of data obtained by liquid scintillation counting of whole sections. Ethopropazine inhibited binding of $^3$H-TCP with a $K_i$ value of 13.80 μM.

In summary, ethopropazine effectively inhibited binding of $^3$H-TCP and was an effective antagonist for NMA neurotoxicity at the following concentrations:

| | vs. NMA Toxicity | $K_i$ vs. $^3$H—TCP |
|---|---|---|
| Ethopropazine | 25.0 μM | 13.80 μM |

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 10 mg per kilogram of body weight per day. A more preferred dosage will be a range from about 0.2 mg to about 5 mg per kilogram of body weight. Most preferred is a dosage in a range from about 0.3 to about 2.5 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effectes. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a disposition of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method to inhibit neurol damage in mammals induced by anoxia, hypoxia or ischemia, which method comprises treating a susceptible mammal with a therapeutically-effective amount of a phenothiazine derivative of the formula

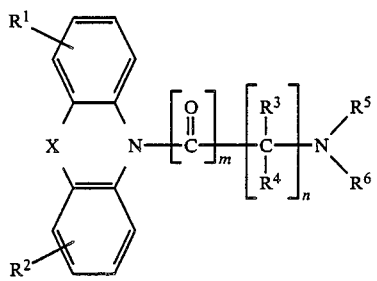

wherein each of $R^1$ and $R^2$ is one or more groups independently selected from hydrido, hydroxyalkyl, haloalkyl, acyl, cycloalkyl, cycloalkylalkyl, haloalkylsulfonyl, alkylcarbonyl, halo, alkylthio, phenylalkyl, phenylalkylthio, cyano, nitro, amino, alkylamino, sulfono, alkylaminosulfonyl, amido, alkylamido, hydroxyimino, hydroxyiminoalkyl, carboxyl, carboxyalkyl, carboxyalkenyl, alkoxycarbonylamino, alkylaminosulfonylamino, aminocarbonyliminoalkyl, haloalkylcarbonyl, cyclopropylcarbonyl, iminoalkyl and hydroxyiminoalkyl; wherein each of $R^3$ through $R^6$ is independently selected from hydrido, alkyl, alkoxy, alkenyl, hydroxyalkyl, alkylaminoalkylcarbonyl, alkoxyalkyl, glycyl, aminoalkyl, alkylaminothioalkyl, aminoalkylcarbonyloxy, cyano, phenylalkyl, phenylalkyloxyalkyl, cycloalkyl, haloalkyl, phenylalkylaminoalkylamido and alkylaminocarbonyloxyalkyl; wherein X is selected from sulfur, sulfinyl and sulfonyl; wherein m is zero or one; and wherein n is an integer from one through five.

2. The method of claim 1 wherein each of $R^1$ and $R^2$ is one or more groups independently selected from hydrido, alkyl, alkoxy, hydroxyl, aldehyde, hydroxyalkyl, haloalkyl, acyl, cycloalkyl, cycloalkylalkyl, haloalkylsulfonyl, alkylcarbonyl, halo, alkylthio, phenalkyl, phenalkylthio, nitro, amino, alkylamino, sulfono, alkylaminosulfonyl, amido, alkylamido, hydroxyimino, hydroxyiminoalkyl, carboxyl, carboxyalkyl, carboxyalkenyl, alkoxycarbonylamino, alkylaminosulfonylamino, aminocarbonyliminoalkyl, haloalkylcarbonyl, cyclopropylcarbonyl, iminoalkyl and hydroxyiminoalkyl; wherein each of $R^3$ and $R^4$ is independently selected from hydrido, alkyl, alkoxy, alkenyl, hydroxyalkyl, alkylaminoalkylcarbonyl, alkoxyalkyl, glycyl, aminoalkyl, haloalkyl, alkylaminothioalkyl, aminoalkylcarbonyloxy and cyano; wherein each of $R^5$ and $R^6$ is independently selected from hydrido, alkyl, alkoxy, hydroxyalkyl, benzyl, haloalkyl, alkoxyalkyl, alkoxycarbonyl, cycloalkyl, alkenyl, phenylalkoxyalkyl, phenylalkylaminoalkylamido and alkylaminocarbonyloxyalkyl; wherein X is sulfur; wherein m is zero or one; and wherein n is an integer from one through four.

3. The method of claim 2 wherein each of $R^1$ and $R^2$ is one or more groups independently selected from hydrido, alkyl, alkoxy, hydroxyl, hydroxyalkyl, haloalkyl, alkylthio, alkoxycarbonyl, cyano, amino and alkylamino; wherein each of $R^3$ and $R^4$ is independently selected from hydrido, alkyl, hydroxyalkyl, alkenyl, haloalkyl, aminoalkyl and cyano; wherein each of $R^5$ and $R^6$ is independently selected from hydrido, alkyl, haloalkyl, cycloalkyl, benzyl, and alkoxyalkyl; wherein m is zero; wherein X is sulfur; and wherein n is an integer from one through three.

4. The method of claim 3 wherein each of $R^1$ and $R^2$ is one or more groups independently selected from hydrido, methyl, ethyl, n-propyl, isopropyl, n-butyl, sec-butyl, iso-butyl, tert-butyl, acetyl, trifluoromethyl, methoxycarbonyl and ethoxycarbonyl; wherein each of $R^3$ and $R^4$ is independently selected from hydrido, methyl, ethyl, n-propyl, isopropyl, n-butyl, sec-butyl, iso-butyl, tert-butyl, hydroxyethyl, trifluoromethyl, 2,2,2-trifluoroethyl, perfluorethyl, aminomethyl and aminoethyl; wherein each of $R^5$ and $R^6$ is independently selected from hydrido, methyl, ethyl, n-propyl, isopropyl, n-butyl, sec-butyl, iso-butyl and tert-butyl; wherein X is sulfur; wherein m is zero; and wherein n is one or two.

5. The method of claim 4 wherein each of $R^1$ and $R^2$ is hydrido; wherein each of $R^3$ and $R^4$ is independently selected from hydrido, methyl and ethyl; wherein each of $R^5$ and $R^6$ is independently selected from methyl, ethyl and n-propyl; wherein X is sulfur; wherein m is zero; and wherein n is two.

6. The method of claim 1 wherein said compound is selected from
10-[2-(dimethylamino)propyl]phenothiazine;
10-[2-(diethylamino)ethyl]phenothiazine;
10-[2-(diethylamino)ethyl]phenothiazine hydrochloride;
10-[2-(dimethylamino)propyl]phenothiazine hydrochloride;
10-[2,3-bis(dimethylamino)propyl]phenothiazine;
10-[2-(dimethylamino)propyl]phenothiazine;
N-(diethylaminoethyl)thiodiphenylamine;
2-propionyl-10-[2-dimethylamino)propyl]phenothiazine;
10-[2-(dimethylamino)ethyl]-2-(trifluoromethyl)phenothiazine;
10-(N,N-dimethylglycyl)phenothiazine;
2-chloro-10-[2-(dimethylamino)propyl]phenothiazine;
10-[(diethylamino)acetyl]-10H-phenothiazine;
N,N,α-trimethyl-2-(methylthio)thiophenothiazine-10-acetamide;
2-cyclopropyl-10-[2-(diethylamino)ethyl]phenothiazine;
10-[2-[methyl(α-methylphenethyl)amino]ethyl]phenothiazine;
2-(cyclopropylmethyl)-10-(N,N-dimethylglycyl)-phenothiazine maleate;
10-[2-(diethylamino)ethyl]-2-[(trifluoromethyl)sulfonyl]phenothiazine;
10-[2-[[2-(benzyloxy)ethyl]ethylamino]ethyl]-2-(trifluoromethyl)phenothiazine;
2-chloro-β-[(dimethylamino)methyl]-phenothiazine-10-ethanol monohydrochloride;
2-cyclopropyl-N,N,α-trimethyl-10H-phenothiazine-10-ethanamine;
2-[ethyl[2-[2-(trifluoromethyl)phenothiazin-10-yl]ethyl]amino]ethanol;
10-(N,N-dimethylnorleucyl)phenothiazine;
N,N,α-trimethyl-2-[(2-methylpropyl)thio]-10H-phenothiazine-10-ethanamine;
10-[2-(dimethylamino)ethyl]-2-(isopropylthio)phenothiazine;
10-[2-(dimethylamino)ethyl]-2-(ethylthio)phenothiazine;
2-(butylthio)-N,N-diethyl-α-methyl-10H -phenothiazine-10-ethanamine hydrochloride;
N,N,α-trimethyl-2-[(phenylmethyl)thio]-10H -phenothiazine10-ethanamine;
10-[2-(dimethylamino)propyl]-N,N-dimethyl-10H-phenothiazine-3-sulfonamide;

10-[2-(dimethylamino)propyl]-phenothiazine 5oxide monohydrochloride;
10-[2-(dimethylamino)-1-methylethyl]-phenothiazine monomethosulfate;
1-[10-[2-(dimethylamino)-1-methylethyl]phenothiazin-3-yl]-1-propanone hydrochloride;
N,N,β-trimethyl-10H-phenothiazine-10-ethanamine diethyl sulfate;
10-(N,N-dimethyl-2-phenylglycyl)phenothiazine;
3,7-dibromo-10-[2-(dimethylamino)propyl]phenothiazine5,5-dioxide;
3,7-dibromo-10-[2-(dimethylamino)ethyl]-phenothiazine5,5-dioxide;
10-[2-(dimethylamino)ethyl]-7-nitro-phenothiazin-3-ol-5,5-dioxide;
10-[2-(dimethylamino)ethyl]-7-hydroxy-phenothiazine-3-sulfonic acid-5,5-dioxide;
2,2'-[(2-phenothiazin-10-ylethyl)imino]di-ethanol;
N,N-diethyl-1-phenothiazin-10-ylthio-formamide;
10-[2-(dimethylamino)propyl]-N,N-dimethyl-10-H-phenothiazine-2-sulfonamine methanesulfonate;
10-[2-(dimethylamino)propyl]-2-methoxy-phenothiazine5-oxide;
10-[2-(dimethylamino)propyl]-2-methoxyphenothiazine;
10-[2-(dimethylamino)ethyl]-N,N-dimethylphenothiazine-2-sulfonamide maleate;
10-[2-(dimethylamino)ethyl]-2-phenothiazinecarbonitrile;
10-[2-(dimethylamino)ethyl]-2-phenothiazinecarbonitrile 5-oxide;
10-[2-(dimethylamino)propyl]phenothiazine-2-carbonitrile;
10-[2-(dimethylamino)-1-methylethyl]-phenothiazine-5,5-dioxide;
10-[2-(dimethylamino)propyl]-phenothiazine-2-sulfonamide;
1-[10-[2-(dimethylamino)ethyl]phenothiazin-3-yl-1-butanone;
ethyl methyl(2-phenothiazin-10-ylpropyl)carbamate-S,S-dioxide;
10-[2-(dimethylamino)propyl]-phenothiazine-5,5-dioxide tartrate;
10-[2-(dimethylamino)propyl]-N,N-dimethyl-phenothiazine-2-sulfonamide oxide;
10-[2-[bis(2-chloroethyl)amino]ethyl]-3-methoxyphenothiazine monohydrochloride;
N,N-diethyl-phenothiazine-10-carboxamide;
10-[2-(dimethylamino)ethyl]-phenothiazine-2-acetic acid monohydrochloride;
2-chloro-N-methyl-N-[2-[methyl(2-phenylethyl)amino[ethyl]-10H-phenothiazine-10-carboxamide;
10-[2-(dimethylamino)propyl]-10H -phenothiazine-2-carboxaldehyde;
N,N-diethyl-3-methyl-10H-phenothiazine-10-ethanamine monohydrochloride;
N,N-bis[2-[[(methylamino)carbonyl]oxy]ethyl]-10H-phenothiazine-10-carboxamide;
methyl[10-[2-(dimethylamino)ethyl]-10H -phenothiazin-2yl]carbamate;
N'-[10-[2-(dimethylamino)propyl]-10H -phenothiazin-2-yl]N,N-dimethyl-sulfamide;
3-[10-[2-(dimethylamino)propyl]-10H-phenothiazin-2-yl]-2-propenoic acid;
2-(cyclopropylmethyl)-10-[2-(dimethylamino)ethyl]-phenothiazine;
10-[2-(dimethylamino)ethyl]-1-ethyl-phenothiazine;
10-[2-(dimethylamino)ethyl]-N-methyl-phenothiazine-2-carboxamide;
1-[10-[2-(dimethylamino)propyl[phenothizin-2-yl]-1-propanone;
10-[2-(dimethylamino)ethyl]-N-ethyl-phenothiazine-2-carboxamide;
10-[2-(dimethylamino)propyl]-2-(methylthio)phenothiazine;
10-[2-(dimethylamino)propyl]-phenothiazine-2-carboxaldehyde;
2-tert-butyl-10-[2-(dimethylamino)-1-methylethyl]-phenothiazine;
10-[2-(dimethylamino)ethyl]-2-pentylphenothiazine;
10-[2-(dimethylamino)-1,1-dimethylethyl]-2-(methylthio)phenothiazine;
10-[N-[2-(dimethylamino)ethyl]sarcosyl]phenothiazine;
10-[2-(dimethylamino)propyl]phenothiazine-2-carboxaldehyde semicarbazone;
chloromethyl 10-[2-(dimethylamino)ethyl]phenothiazin-2-yl-ketone hydrochloride;
cyclopropyl 10-[2-(dimethylamino)propyl]phenothiazin-2-yl-ketone methiodide;
10-[2-(dimethylamino)propyl]-α,α-dimethyl-10H-phenothiazine-2-acetonitrile;
10-(2-dimethylaminoethyl)phenothiazin-2-yl methylketoneoxime;
β-dimethylaminophenothiazine-10-butyronitrile;
10-[2-(diallylamino)ethyl]phenothiazine;
2-(dimethylamino)-10-[2-(dimethylamino)ethyl]phenothiazine maleate;
10-(2-dimethylamino-1-methylethyl)-2-phenylphenothiazine;
N,N-dicyclohexyl-phenothiazine-10-carboxamide;
10-(2-diethylaminoethyl)-2,8-dimethoxyphenothiazine;
2-chloro-10-[2-[(4-ethoxybutyl)ethylamino]ethyl]-phenothiazine;
10-[2-(dimethylamino)propyl]-a,α-dimethyl-10H-phenothiazine-2-acetic acid monohydrochloride.

7. The method of claim 6 wherein said compound is selected from
10-[2,3-bis(dimethylamino)propyl]phenothiazine;
10-[2,3-bis(dimethylamino)propyl]phenothiazine hydrochloride;
10-[2-(dimethylamino)propyl]phenothiazine; and
10-[2-(dimethylamino)propyl]phenothiazine hydrochloride;
10-[2-(diethylamino)ethyl]phenothiazine.

8. The method of claim 7 wherein said compound is 10-[2-(diethylamino)ethyl]phenothiazine or its hydrochloride salt.

* * * * *